United States Patent [19]

Schrenk et al.

[11] 4,393,139
[45] Jul. 12, 1983

[54] PROCESS FOR THE SELECTIVE SEPARATION OF ENDOPROTEASES

[75] Inventors: Jürgen Schrenk, Weilheim; Peter Wunderwald, Haunshofen, both of Fed. Rep. of Germany

[73] Assignee: Boehringer Mannheim GmbH, Mannheim-Waldhof, Fed. Rep. of Germany

[21] Appl. No.: 297,467

[22] Filed: Aug. 28, 1981

[30] Foreign Application Priority Data

Sep. 10, 1980 [DE] Fed. Rep. of Germany ....... 3034043

[51] Int. Cl.³ .................... C12N 9/50; C12N 9/48; C12N 9/60
[52] U.S. Cl. .................... 435/219; 435/212; 435/224; 435/814; 252/430
[58] Field of Search ............... 435/212–226, 435/814

[56] References Cited

PUBLICATIONS

Trends in Biochemical Sciences (TIBS), vol. 5, pp. 43–47, 1980.
Analytical Biochemistry, vol. 99, pp. 415–420, (1979).
Biochemical Journal, vol. 133, pp. 709–724, (1973).
Methods in Enzymology, vol. XLV, pp. 639–652, (1976).

Primary Examiner—Lionel M. Shapiro
Attorney, Agent, or Firm—Felfe & Lynch

[57] ABSTRACT

The present invention provides a process for the selective separation of endoproteases from aqueous solutions, wherein an aqueous solution containing proteases is treated with a complex, present in the solid phase, of alpha$_2$-macroglobulin with a divalent metal selected from zinc, cobalt, nickel and copper and the solid phase then separated off.

The present invention also provides an agent for carrying out this process, wherein it comprises a solid carrier material which is loaded with a complex of alpha$_2$-macroglobulin and of a divalent metal selected from zinc, cobalt, nickel and copper.

5 Claims, No Drawings

PROCESS FOR THE SELECTIVE SEPARATION OF ENDOPROTEASES

This invention relates to the selective separation of endoproteases from aqueous solutions and especially with their separation from other biologically-active proteins in aqueous solutions.

Endoproteases and proteolytic enzymes which hydrolize proteins at particular peptide bonds in the middle of the chain but do not attack the ends of the chain. Examples of endopeptidases include pepsin, trypsin, chymotrypsin, collagenase, papain, ficin, clostripain, subtilisin, elastase and bromelain and numerous others.

A particular problem is the presence of such endoproteinases in the case of processes for obtaining biologically-active proteins, especially when a biological starting material is used which is relatively rich in such endoproteinases. Since these endoproteinases are frequently very difficult to separate from other proteins and the purification and fractionation of biologically-active proteins usually takes place under conditions under which the endoproteases are active, the latter very considerably disturb the purification of the other biologically-active proteins and are largely responsible for the losses of biological activity which usually occur in the case of such purification operations. Therefore, a process which enables the selective separation of endoproteinases would substantially improve the practicability of many methods for the purification of bilogically-active proteins.

Although there is a need for such a process for the specific separation of endoproteinases from aqueous solutions, it has hitherto not been possible to find such a process which is generally satisfactory. This problem is solved by the present invention.

Thus, according to the present invention, there is provided a process for the selective separation of endoproteases from aqueous solutions, wherein an aqueous solution containing proteases is treated with a complex, present in the solid phase, of alpha$_2$-macroglobulin with a divalent metal selected from zinc, cobalt, nickel and copper and the solid phase then separated off.

The endoproteinases are selectively fixed on to the alpha$_2$-macroglobulin-metal chelate complex and can be separated from the aqueous solution with the solid phase.

Alpha$_2$-macroglobulin and its properties are known, for example, from TIBS, 5, 43–47/1980. Alpha$_2$-macroglobulin, hereinafter referred to as $\alpha_2$M, is a universal protease inhibitor of which it is known that it forms a complex with the proteases in the case of which it undergoes a drastic change in its structure (see, for example, FIG. 1 in TIBS, loc. cit.).

Furthermore, it is known from Anal. Biochem., 99, 415–420/1979 that $\alpha_2$M can be purified over a column with carrier-bound zinc chelate. It was thereby observed that no $\alpha_2$-M-protease complexes occurred suggesting that the change of structure of the $\alpha_2$-M molecule necessary for the protease binding interferes with the bonding on to the metal chelate.

Surprisingly, however, we have now found that endoproteases nevertheless bind selectively on to $\alpha_2$M-metal chelate complexes of certain metals and, in this way, can be separated from accompanying substances and especially from other proteins. Thus, their ascertainment contradicts the previous knowledge of the properties of $\alpha_2$M.

The process according to the present invention can be used for the selective separation of all endoproteinases which are also inhibited by $\alpha_2$M. Thus, it also permits the separation of endoproteinases which are inhibited by $\alpha_2$M from those endoproteinases which are not inhibited by $\alpha_2$M.

The carrier material for the solid phase may, in particular, be a cation exchanger which is able to bind the above-mentioned group of divalent metals. Preferred cation exchangers are those which carry a carboxymethylamino radical, for example carboxymethylaminoagarose, or iminoacetic acid-sepharose.

The preparation of the complex of $\alpha_2$M and divalent metal present in the solid phase and used according to the present invention may be carried out, according to one embodiment of the present invention, by dissolving the $\alpha_2$M in an aqueous solution containing the endoproteinases to be separated and then treating this solution with a cation exchanger which is loaded with the divalent metal, i.e. with zinc, cobalt, nickel and/or copper. On the other hand, it is also possible first to contact the $\alpha_2$M in solution with a cation exchanger loaded with the divalent metal, the $\alpha_2$M thereby being bonded to the solid phase, and subsequently to mix the solid phase with the protease-containing solution.

Regardless of which of the two above-described embodiments of the present invention is used, the protease-containing solution can be chromatographed over the solid phase or the protease-containing solution can simply be mixed with the solid phase and subsequently again removed therefrom (batch process). As can be seen from the above-described first embodiment of the present invention, the already-formed complex of $\alpha_2$M-endoprotease is also fixed on to the carrier-bond divalent metal. The bonding is quantitative and the solution treated according to the present invention is subsequently free of endopeptidases which can be inhibited by $\alpha_2$M.

For the regeneration of the solid phase, it is washed with salt solutions of appropriate concentration. Thus, for example, there can be used 0.05 to 0.5 M and preferably 0.08 to 0.2 M aqueous sodium acetate solution with a pH of 4 to 5 and preferbly of 4.3 to 4.7, with a content of 0.5 to 1 M and preferably of 0.7 to 0.9 M sodium chloride. Another example of a regeneration solution is a 0.5 to 2 N aqueous solution of sodium hydroxide. Furthermore, use can also be made of a 0.01 to 2.0 M and preferably 0.02 to 0.05 M dimethylarsine buffer with a pH of 4 to 6 and preferably of 4.7 to 5.3 with a content of 0.1 to 1 M and preferably of 0.5 to 0.8 M sodium chloride. The complex of $\alpha_2$M-endoproteinase eluted in this way can only be broken down by denaturation, for example by reduction.

For the production of the solid metal complex-containing carrier material, a solution of the divalent metal in question in the form of an appropriate salt, preferably as a salt of a mineral acid, for example a sulphate or chloride, is brought together with a cation exchanger and preferably with a cation exchanger resin. The concentration of the metal salt solution is preferably 3 to 8 mg./ml. and the pH should be from 4 to 6.5. However, solutions outside the given range can also be used although losses can hereby occur and the purification can be made difficult. After binding the metal ions on to the carrier, it is preferable to wash thoroughly with a buffer solution, for example with 2 to 10 volumes of 0.05 to 0.5 M acetate buffer which contains 0.1 to 0.5 M sodium chloride and has a pH of from 4 to 6.

If the $\alpha_2$M as such is to be bound to the carrier, then it is preferably used in the form of a solution in an appropriate buffer. In general, there are used buffer concentrations of from 0.01 to 0.05 M and preferably of 0.02 to 0.03 M. The pH value should be from 5.5 to 9 and preferably from 6.0 to 8. All buffer substances which buffer in this range can be used, although sodium and potassium phosphate buffers are preferred. In general, 10 to 100 U of $\alpha_2$M can be fixed per ml. of carrier volume.

The endoproteinase-containing solution should have a pH of from 6 to 8.5 and the salt content should not exceed 0.3 M. As buffer substances, there can again be used all those which buffer in this range, phosphate buffer and tris buffer being preferred.

If the process according to the present invention is carried out by first mixing the endoproteinase-containing solution to be treated with $\alpha_2$M and only subsequently passing the solution over the metal chelate-containing carrier, then the above statements apply correspondingly with regard to the salt concentration, the pH value and the buffer substances.

The process according to the present invention makes it possible to remove disturbing endoproteinases quickly and simply from solutions containing them and, in this way, especially to protect biologically-active proteins against loss of activity due to the action of endoproteinases or to stabilise biologically-active proteins. Furthermore, the process according to the present invention can also be used for separating endoproteases which can be inhibited by $\alpha_2$M from other endoproteases and exoproteases.

The present invention also provides an agent for carrying out the process according to the present invention, which agent comprises a solid carrier material loaded with a complex of $\alpha_2$M and of a divalent metal selected from zinc, cobalt, nickel and copper. The carrier is preferably a cation exchanger resin and more preferably agarose containing carboxymethylamino radicals. However, other carrier materials such as are conventionally used for fixing biologically-active proteins, can also be employed in the same way. The only important characteristic is that they take up divalent metal ions.

The following Examples are given for the purpose of illustrating the present invention:

EXAMPLE 1

Bis-(carboxymethylamino)-agarose is loaded with five times its volume of zinc chloride solution (3 mg./ml., pH 6.3) and subsequently washed with 3 times its volume of acetate buffer (0.05 M sodium acetate+0.15 M sodium chloride, pH 5.0). $\alpha_2$M is then absorbed on to this zinc chelate carrier in phosphate buffer (0.02 M sodium phosphate+0.15 M sodium chloride, pH 6.0). The so obtained column of $\alpha_2$M is then washed with 10 to 15 times its volume of phosphate buffer.

2 ml. dialysed yeast extract in 0.05 M potassium phosphate (pH 7.0)+$10^{-3}$ M ethylenediamine-tetraacetic acid +$10^{-3}$ MCE are then chromatographed over 1 ml. of this absorbent. The flow through is made 1 mM in ethylene-diamine-tetraacetic acid, 0.2 mM in azide, and 50% in glycerol. The $\alpha$-glucosidase activity after 11 days at 33° C. is 100% (untreated control 73%) and after 19 days at 33° C. is still 92% (untreated control 32%). The $\alpha$-glucosidase test is carried out in the manner described in H. U. Bergmeyer's Methoden der enzymatischen Analyse, pub. Verlag Chemie, Weinheim/Bergstrasse, p. 488/1974.

EXAMPLE 2

A preparation from 206 liters of culture filtrate of *Lysobacter enzymogenes* ssp. *enzymogenes*, DSM 1895 (ATCC 27996) pre-purified by ammonium sulphate fractionation and "Sephadex" G-100 chromatography (this process is described in more detail in Federal Republic of Germany Patent Specification No. 30 34 045), which contains various endoproteinases which can be inhibited by $\alpha_2$M, is treated with the $\alpha_2$M-zinc complex described in Example 1. For this purpose, 110 ml. of this carrier material are packed into a column of 3 cm. diameter and 17.5 cm. length and washed with 0.05 M tris buffer (pH 8.0) until there is no protein in the eluate. The pre-purified culture filtrate preparation is then applied to the column and subsequently washed with 0.05 M tris buffer (pH 8.0). Only the Lys-C-proteinase, which has hitherto not been described, passes through, all the other proteinases being retained.

It will be understood that the specification and examples are illustrative but not limitative of the present invention and that other embodiments within the spirit and scope of the invention will suggest themselves to those skilled in the art.

We claim:

1. Process for the selective separation of endoproteases from aqueous solutions, which process comprises treating an aqueous solution containing proteases with a complex, present in the solid phase, of alpha$_2$-macroglobulin with a divalent metal selected from zinc, cobalt, nickel and copper, and then separating off the solid phase containing endoprotease inhibited by alpha$_2$-macroglobulin.

2. Process as claimed in claim 1, wherein the alpha$_2$-macroglobulin is dissolved in the aqueous solution and the solution obtained treated with a cation exchanger which is loaded with the divalent metal.

3. Process as claimed in claim 1, wherein the alpha$_2$-macroglobulin is contacted with a cation exchanger loaded with the divalent metal and then mixed with the protease-containing solution.

4. Process as claimed in claim 1, wherein the protease-containing solution is chromatographed over the solid phase.

5. Process as claimed in claim 1, wherein the solid phase is added to the protease-containing solution and thereafter again removed therefrom.